United States Patent [19]

Loder, Jr. et al.

[11] 3,976,439
[45] Aug. 24, 1976

[54] NON-LEADED GASOLINE HAVING IMPROVED ANTI-KNOCK QUALITY

[75] Inventors: Wallace R. Loder, Jr., North Olmsted; Philip S. Fay, Lyndhurst; Franklin Veatch, University Heights, all of Ohio

[73] Assignee: Standard Oil Company, Cleveland, Ohio

[22] Filed: Sept. 24, 1975

[21] Appl. No.: 616,389

[52] U.S. Cl. ............................... 44/68; 260/429 K; 260/429 R; 260/429.9; 260/439 R; 260/438.1
[51] Int. Cl.² .......................................... C10L 1/24
[58] Field of Search ......... 44/68; 260/429 R, 439 R, 260/438.1, 429.9, 429 K

[56] References Cited
UNITED STATES PATENTS

| | | | |
|---|---|---|---|
| 2,777,874 | 1/1957 | Asseff et al. | 260/429 X |
| 3,794,473 | 2/1974 | Eisentraut et al. | 44/68 |
| 3,880,900 | 4/1975 | Fujii et al. | 260/429 K |

*Primary Examiner*—Daniel E. Wyman
*Assistant Examiner*—Y. Harris-Smith
*Attorney, Agent, or Firm*—John F. Jones; Sherman J. Kemmer

[57] ABSTRACT

Non-leaded motor fuel compositions having improved octane rating N,N-disubstituted diselenocarbamates of certain metals as octane improvers.

7 Claims, No Drawings

NON-LEADED GASOLINE HAVING IMPROVED ANTI-KNOCK QUALITY

This invention relates to improved hydrocarbon fuel compositions and more particularly pertains to improved non-leaded motor gasoline fuel compositions having improved octane numbers.

Recent automotive design trends have been toward engines having greater power for the same size engine and more efficient utilization of the gasoline fuel. Environmental considerations have resulted in legislation setting limits on the amounts and types of auto exhaust emissions. The requirements for catalytic mufflers in auto exhaust systems have necessitated the adoption of non-leaded gasoline in autos produced after 1975. This in turn has created a need for non-lead octane improvers for the production of acceptable lead-free gasoline fuels.

We have discovered that N,N-disubstituted diselenocarbamates of certain metals are excellent anti-knock additives for non-leaded gasoline. These useful anti-knock compounds generally conform to the formula

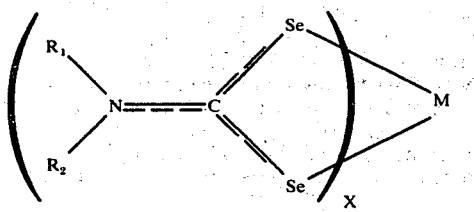

wherein M is a metal selected from the group consisting of nickel, zinc, copper, manganese and iron, X is the valence state of the metal, and $R_1$ and $R_2$ are alkyl, cycloalkyl, or aryl groups. These compounds can be prepared from carbon diselenide, a secondary amine and a salt of the metal. The longer the alkyl chain, the lower the melting point and the higher the fuel solubility will be for the particular N,N-disubstituted diselenocarbamates of this invention.

A useful concentration range for the octane improvers of this invention is from 0.0625 to 1.0 grams (of metal) per gallon of gasoline. The octane response to a given additive, of course, is dependent on the octane level of the base fuel.

The base gasoline stock useful in this invention can comprise a mixture of hydrocarbons boiling in the gasoline range and can be either a straight-run gasoline or a gasoline obtained from a conventional cracking process, or mixtures thereof. The base gasoline may also contain components from various other refinery processes, such as alkylation, isomerization, hydrogenation, polymerization, catalytic reforming, or combinations of two or more of such processes.

It is intended that the motor fuel of this invention may also include other known additives for commercial fuels, such as detergents, oxidation inhibitors, gum inhibitors deicers, dyes, solvent oils, and the like.

In order to determine the effect of the N,N-disubstituted diselenocarbamates on the octane rating of the unleaded fuel, blended fuels were evaluated in the standard ASTM (research) and ASTM (motor) octane test procedures.

The following examples will further illustrate the invention.

EXAMPLE A

The N,N-disubstituted diselenocarbamates were prepared as follows:

Into a 250-ml. three-neck round-bottom flask equipped with nitrogen outlet, thermometer, magnetic stirrer, and a 125-ml. pressure equalizing addition funnel containing a nitrogen inlet were charged 1.2 grams of sodium hydroxide, 40 ml. of distilled water and 2.2 grams of dipentyl amine. A stream of nitrogen then was used to flush out the system; the nitrogen outlet being connected to a bubbler containing 20% alcoholic potassium hydroxide. A solution of 4.2 grams of carbon diselenide in 40 ml. of p-dioxane was placed in the addition funnel. The flask was cooled to −10°C by means of a dry ice-acetone bath. The nitrogen flow was set at such a rate that an occasional bubble was observed in the bubbler. The carbon diselenide solution was added over a 2-hour period with vigorous stirring. After the addition was complete, the stirring was continued until the solution warmed to about 10°–15°C in the absence of the cold bath. The resulting dark-amber solution was centrifuged to remove insoluble materials and was then recooled to 0°C.

A solution of 0.015 mole of a divalent metal salt (i.e., $NiCl_2$) in 10 ml. of distilled water and 125 ml. of benzene was vigorously stirred at 5°C in a 500-ml. erlenmeyer flask, and the above prepared ligand solution was added over a 5-minute period. The resulting mixture was stirred vigorously for 10 to 15 minutes and was filtered. The organic layer was then separated and washed with five 50-ml. portions of distilled water. The benzene solution was dried overnight over sodium sulfate, then filtered and benzene removed by evaporation leaving a residue (oil or solid depending on metal salt used). The oils were dried at 30–50 microns of vacuum at 45°C for 3 hours. The solids were recrystallized from n-heptane. Table 1 lists the various N,N-dialkyl diselenocarbamate metal chelates prepared in this manner.

Table 1

| Chelate | % Metal | % Se | Color | M.P. |
|---|---|---|---|---|
| bis(N,N-diethyl diseleno-carbamato) nickel II | 10.82 | 58.18 | green-black | 270–3°C |
| bis(N,N-dipentyl diseleno-carbamato) nickel II | 8.26 | 44.41 | light brown | 59–62°C |
| bis(N,N-dipentyl diseleno-carbamato) zinc II | 9.11 | 44.00 | colorless | oil |
| bis(N,N-dipentyl diseleno-carbamato) copper II | 8.87 | 44.11 | purple | oil |
| tris(N,N-dipentyl diseleno-carbamato) manganese III | 5.32 | 45.84 | red | oil |
| tris(N,N-dipentyl diseleno-carbamato) iron III | 5.40 | 45.80 | brown-black | dec. 120°C |

EXAMPLE B

The physical and chemical properties of the base fuel employed in the octane test program were as follows:

| distillation | °F |
|---|---|
| initial boiling point | 90 |
| 10% | 127 |
| 50% | 236 |
| 90% | 334 |
| E. P. | 406 |
| percent recovered | 95 |
| percent residue | 1 |
| percent loss | 4 |
| gravity, °API | 56.5 |
| RVP, psig | 9.3 |
| octane ASTM research | 93.2 |

-continued

| | | |
|---|---|---|
| octane ASTM motor | | 85.2 |
| composition | | |
| | light cat. dist. | 15% |
| | light cat. ref. | 5% |
| | heavy cat. ref. | 15% |
| | total cat. ref. | 32% |
| | light isocrackate | 22% |
| | motor alkylate | 11% |
| FIA, | % aromatic | 27.2 |
| | % olefins | 2.4 |
| | % saturates | 70.4 |

Table 2 shows the results of using varying amounts of the metal chelates described in Example A in the base fuel.

Table 2

| Ex. | Metal Chelate | Conc. Grams of Metal/ Gallon | Change in Octane Number Over Base Fuel | |
|---|---|---|---|---|
| | | | Research | Motor |
| 1 | nickel II | 0.125 | 0.2 | 0.7 |
| 2 | " | 0.250 | 0.8 | 1.4 |
| 3 | " | 0.500 | 1.4 | 1.7 |
| 4 | " | 1.000 | 2.6 | 2.6 |
| 5 | zinc II | 0.125 | 0.0 | −0.4 |
| 6 | " | 0.250 | 0.2 | 0.0 |
| 7 | " | 0.500 | 0.5 | 0.6 |
| 8 | " | 1.000 | 1.4 | 0.9 |
| 9 | copper II | 0.125 | −0.5 | −0.5 |
| 10 | " | 0.250 | −0.3 | −0.4 |
| 11 | " | 0.500 | 0.4 | −0.2 |
| 12 | " | 1.000 | 1.4 | 2.2 |
| 13 | manganese III | 0.125 | 0.2 | −0.4 |
| 14 | " | 0.250 | 0.6 | −0.2 |
| 15 | " | 0.500 | 1.8 | 0.9 |
| 16 | " | 1.000 | 3.6 | 3.6 |
| 17 | iron III | 0.125 | 0.4 | −0.9 |
| 18 | " | 0.250 | 0.9 | −0.2 |

Table 2-continued

| Ex. | Metal Chelate | Conc. Grams of Metal/ Gallon | Change in Octane Number Over Base Fuel | |
|---|---|---|---|---|
| | | | Research | Motor |
| 19 | " | 0.500 | 1.2 | 0.8 |

We claim:
1. A non-leaded gasoline composition for internal combustion engines containing from about 0.0625 to 1.0 grams of metal per gallon of fuel of a compound having the formula

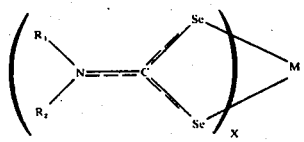

wherein M is a metal selected from the group consisting of nickel, zinc, copper, manganese, and iron, X is the valence state of the metal, and $R_1$ and $R_2$ are alkyl, cycloalkyl or aryl groups.
2. The motor fuel of claim 1 wherein $R_1$ and $R_2$ are alkyl groups.
3. The motor fuel of claim 2 wherein the compound is bis(N,N-diethyl diselenocarbamato) nickel II.
4. The motor fuel of claim 2 wherein the compound is bis(N,N-dipentyl diselenocarbamato) nickel II.
5. The motor fuel of claim 2 wherein the compound is bis(N,N-dipentyl diselenocarbamato) copper II.
6. The motor fuel of claim 2 wherein the compound is tris(N,N-dipentyl diselenocarbamato) manganese III.
7. The motor fuel of claim 2 wherein the compound is tris(N,N-dipentyl diselenocarbamato) iron III.

* * * * *